US008192926B2

(12) United States Patent
Debad et al.

(10) Patent No.: US 8,192,926 B2
(45) Date of Patent: Jun. 5, 2012

(54) COMPOSITIONS AND KITS FOR MULTIPLE BIOMARKER EXTRACTION WITH NITROUS ACID

(75) Inventors: Jeff D. Debad, Gaithersburg, MD (US); Cindy V. Ly, Houston, TX (US)

(73) Assignee: Meso Scale Technologies LLC, Gaithersburg, MD (US)

(*) Notice: Subject to any disclaimer, the term of this patent is extended or adjusted under 35 U.S.C. 154(b) by 0 days.

(21) Appl. No.: 11/436,630

(22) Filed: May 19, 2006

(65) Prior Publication Data

US 2006/0210970 A1 Sep. 21, 2006

Related U.S. Application Data

(62) Division of application No. 10/736,899, filed on Dec. 17, 2003, now Pat. No. 7,078,061.

(60) Provisional application No. 60/436,591, filed on Dec. 26, 2002.

(51) Int. Cl.
   - *C12Q 1/70* (2006.01)
   - *G01N 33/569* (2006.01)
   - *C12N 1/06* (2006.01)

(52) U.S. Cl. ............ 435/5; 435/7.34; 435/259; 435/885; 436/808

(58) Field of Classification Search ............. 435/5, 7.34, 435/259, 885; 436/808
See application file for complete search history.

(56) References Cited

U.S. PATENT DOCUMENTS

| | | | |
|---|---|---|---|
| 3,502,779 A | 3/1970 | Dye et al. | |
| 4,168,146 A | 9/1979 | Grubb et al. | |
| 4,235,601 A | 11/1980 | Deutsch et al. | |
| 4,366,241 A | 12/1982 | Tom et al. | |
| 4,446,232 A | 5/1984 | Liotta | |
| 4,618,576 A | 10/1986 | Rosenstein et al. | |
| 4,737,453 A | 4/1988 | Primus | |
| 4,808,524 A | 2/1989 | Snyder et al. | |
| 4,847,199 A | 7/1989 | Snyder et al. | |
| 5,028,535 A | 7/1991 | Buechler et al. | |
| RE33,850 E | 3/1992 | Snyder et al. | |
| 5,334,503 A | 8/1994 | Snyder et al. | |
| 5,364,763 A | 11/1994 | Kacian | |
| 5,374,524 A | 12/1994 | Miller | |
| 5,415,994 A | 5/1995 | Imrich et al. | |
| 5,494,801 A * | 2/1996 | Bogart et al. | 435/7.34 |
| 5,536,646 A | 7/1996 | Sand et al. | |
| 5,707,802 A | 1/1998 | Sandhu et al. | |
| 5,869,272 A | 2/1999 | Bogart et al. | |
| 5,945,526 A * | 8/1999 | Lee et al. | 536/26.6 |
| 5,955,377 A | 9/1999 | Maul et al. | |
| 5,965,375 A | 10/1999 | Valkirs | |
| 5,993,826 A | 11/1999 | Hansen et al. | |
| 6,066,448 A | 5/2000 | Wohlstadter et al. | |
| 6,140,045 A | 10/2000 | Wohlstadter et al. | |
| 6,194,221 B1 | 2/2001 | Rehg et al. | |
| 6,207,369 B1 | 3/2001 | Wohlstadter et al. | |
| 6,207,375 B1 | 3/2001 | Subramaniam et al. | |
| 6,207,445 B1 | 3/2001 | Crosby | |
| 6,238,676 B1 | 5/2001 | Porcelli et al. | |
| 6,248,513 B1 | 6/2001 | Horaud et al. | |
| 6,673,533 B1 | 1/2004 | Wohlstadter et al. | |
| 6,977,722 B2 | 12/2005 | Wohlstadter et al. | |
| 7,015,046 B2 | 3/2006 | Wohlstadter et al. | |
| 7,192,701 B2 | 3/2007 | Lee et al. | |
| 2001/0012537 A1* | 8/2001 | Anderson et al. | 427/2.1 |
| 2001/0021534 A1 | 9/2001 | Wohlstadter et al. | |
| 2003/0113713 A1 | 6/2003 | Glezer et al. | |
| 2004/0022677 A1 | 2/2004 | Wohlstadter et al. | |
| 2004/0086423 A1 | 5/2004 | Wohlstadter et al. | |
| 2004/0175695 A1 | 9/2004 | Debad et al. | |
| 2004/0189311 A1 | 9/2004 | Glezer et al. | |
| 2005/0052646 A1 | 3/2005 | Wohlstadter et al. | |
| 2006/0068499 A1 | 3/2006 | Wohlstadter et al. | |
| 2007/0166835 A1 | 7/2007 | Bobrow et al. | |
| 2008/0199851 A1 | 8/2008 | Egan et al. | |
| 2008/0213814 A1 | 9/2008 | Gerion et al. | |

FOREIGN PATENT DOCUMENTS

| | | |
|---|---|---|
| EP | 0153477 B1 | 7/1987 |
| WO | WO 95/04280 | 2/1995 |

OTHER PUBLICATIONS

Microbiology 3d Ed., G. A. Wistreich and M. D. Lechtman, eds., Glencoe Publishing Co., Inc., Encino, California, 1980, pp. 600-606.*

U.S. Appl. No. 10/185,274 of Wohlstadter et al., filed Jun. 28, 2002.

U.S. Appl. No. 10/185,363 of Wohlstadter et al., filed Jun. 28, 2002.

Dumbler et al. "Molecular diagnostics for existing and emerging infections" Am. J. Clin. Pathol. 112 (suppl. 1):S33-S39 (1999).

Facklam et al. "Screening for *Streptococcal* pharyngitis: Current technology" Infections in Medicine 14:891-898 (1997).

Hafez et al. "Extraction of group A *Streptococcal* M protein with nitrous acid" J. Clin. Microbiol. 14:530-533 (1981).

Leonardi et al. "Comparison of rapid detection methods for influenza A virus and their value in health-care management of institutionalized geriatric patients" J. Clin. Microbiol. 32:70-74 (1994).

Lieberman "Measurement of sputum viscosity in a cone-plate viscometer" Am. Rev. Resp. Dis. 97:662-672 (1968).

Lightowler et al. "Comparative mucolytic studies on dithiothreitol, N-acetyl-cysteine and L-cysteine on human respiratory mucus in vitro and their effects on the rate of flow of mucus in the exposed trachea of the rat on topical application" Arch. Intl. Pharmacodyn. 189:53-58 (1971).

Petts "Evaluation of a modified nitrous acid extraction latex agglutination kit for grouping beta-hemolytic *Streptococci* and *Enterococci*" J. Clin. Microbiol. 33:1016-1018 (1995).

Slifkin et al. "Serogrouping single colonies of beta-hemolytic *Streptococci* from primary throat culture plates with nitrous acid extraction and Phadebact *Streptococcal* reagents" J. Clin. Micro. 12:541-545 (1980).

(Continued)

*Primary Examiner* — Rosanne Kosson
(74) *Attorney, Agent, or Firm* — Nixon & Vanderhye P.C.

(57) ABSTRACT

The present invention is directed to methods for extracting markers from biological samples, and to systems, devices, kits and reagents for use in such methods. The invention is also to methods, kits, reagents and compositions for measuring a plurality of different organism types in a sample. One of the specific advantages of the present invention is the ability to simultaneously extract more than one microorganism or viral particle marker in one volume from a single sample containing a complex biological matrix.

54 Claims, No Drawings

OTHER PUBLICATIONS

Webb et al. "Clinical evaluation of a new mucolytic agent, acetylcysteine" J. Thoracic & Cardiovascular Surgery 44:330-343 (1962).
Product insert for QuickVue by Quidel (2002.
Product insert for RSV Abbott TestPack by Abbott Laboratories (2002).
Product insert for FluoOIA by Biostar, Inc. (2002).
Product insert for Directigen Flu and RSV by Becton Dickinson & Co. (2002).
International Search Report, dated May 26, 2006 for Int'l Appln. No. PCT/US2003/39938.
Supplementary European Search Report for EP 03790511.4 dated Aug. 23, 2007.

* cited by examiner

COMPOSITIONS AND KITS FOR MULTIPLE BIOMARKER EXTRACTION WITH NITROUS ACID

CROSS-REFERENCE TO RELATED APPLICATION

This application is a division of U.S. patent application Ser. No. 10/736,899, filed Dec. 17, 2003 now U.S. Pat. No. 7,078,061, allowed; which claims priority to U.S. Provisional Application No. 60/436,591, filed Dec. 26, 2002; the contents of which are incorporated herein by reference.

FIELD OF THE INVENTION

The present invention is directed to methods for extracting one or more markers from one or more samples, and, preferably, also measuring such markers. The invention also relates to systems, devices, equipment, kits and reagents for use in such methods.

BACKGROUND OF THE INVENTION

Investigators in the early 50's to early 60's recognized that mucus in clinical samples could have adverse effects on clinical measurements carried out on the samples. In order to minimize the effect of mucous viscosity on clinical samples, specific methods and compositions have been developed to liquefy mucous matrices, such as sputum. Such extraction protocols include the use of DNAses (Lieberman, *Amer. Rev. Resp. Disease*, Vol. 97, pp. 662-672 (1968)) or thiol-containing reducing agents such as N-acetyl-L-cysteine (Webb, *J. Thoracic & Cardiovascular Surg.*, Vol. 44, pp. 330-343 (1962)) or dithiothreitol (U.S. Pat. No. 3,502,779 (Mar. 24, 1970)). These reagents have been used alone or in combination (Lightowler & Lightowler, *Arch. In Pharmacodyn.*, Vol. 189, pp. 53-58 (1971)).

There are a number of immunoassay or agglutination test kits for identifying viral particles, which have emerged on the market in recent years (QuickVue by Quidel, RSV Abbott TestPack by Abbott Laboratories, FluOIA by Biostar, Inc., and Directigen Flu and Directigen RSV by Becton Dickinson and Company). Most of the kits available on the market pre-treat clinical samples with a combination of a detergent and a reducing agent to break down the mucous matrix and to solubilize the antigens. Examples of antigen extraction using a combination of detergent and reducing agent are described in U.S. Pat. No. 6,248,513 to Horaud et al.; U.S. Pat. No. 6,207,445 to Crosby; U.S. Pat. No. 6,194,221 to Rehg et al.; U.S. Pat. No. 5,993,826 to Hansen et al.; U.S. Pat. No. 5,995,377 to Maul et al.; U.S. Pat. No. 5,869,272 to Bogart et al.; U.S. Pat. No. 5,415,994 to Imrich et al.; and U.S. Pat. No. 5,334,503 to Snyder et al., each of which are incorporated herein by reference. Alternatively, although rare, organic solvent extractions are also used in the art (U.S. Pat. No. 6,238,676 to Porcelli et al., which is incorporated herein by reference).

The detection of some bacterial strains via the detection of established protein markers can employ similar extraction procedures to those employed for viral particles. For example, to detect *Legionella pneumophilia* by immunochemical means, a swab containing a sputum sample is pretreated with extraction solution containing a Triton X-100 detergent and EDTA in phosphate-buffered saline (U.S. Pat. No. 5,415,994 (May 16, 1995)).

Nitrous acid has been used for the extraction of carbohydrate antigens from the cell wall of *Streptococci* and *Enterococci* (Petts, *J. Clinical Microbiol.*, Vol. 33(4), pp. 1016-18 (1995); Facklam, *Infections in Medicine*, Vol. 14(11), pp. 891-898 (1997)). Additional examples include U.S. Pat. No. 5,494,801 to Bogart et al. and U.S. Pat. No. 5,536,646 to Sand et al., both of which are incorporated herein by reference. Nitrous acid extraction was only used for extracting cell wall-associated carbohydrate markers from these organisms. Nitrous acid extraction was never expected to be useful or successful in extracting other markers such as protein markers or markers from multiple types of microorganisms in a single sample, especially from a sample containing a complex biological matrix, such as a mucous excretion. On the contrary, it would have been expected that the use of nitrous acid would be detrimental to the assay of protein markers. Proteins undergo denitrification (loss of amine groups) when treated with nitrous acid. This decomposition pathway would be expected to lead to denaturation and/or precipitation. It may also change the antigenic properties of the protein (i.e., the antibodies may not be able to bind to the surface of the protein, since antibody binding characteristics change when the amines are removed). The denitrification, denaturation and/or precipitation would be expected to reduce the amount and accessibility of soluble markers, leavings the amount of markers insufficient for analysis. In addition, it is generally accepted in the art that extensive exposure to acidic conditions can adversely affect antigen solubility or the reactivity of the antibodies utilized by detection techniques (U.S. Pat. No. Re. 33,850).

SUMMARY OF THE INVENTION

The invention is directed to novel methods for processing one or more samples for analysis, and to reagents, compositions and kits for use in such methods. More preferably, the invention relates to extraction methods for extracting one or more markers from the matrices of one or more samples (preferably from one or more complex samples such as mucus) and/or for rendering the samples more suitable to analysis (e.g., by decreasing the viscosity of the sample).

Surprisingly, the preferred embodiments of the invention allow for the extraction and measurement of multiple markers from the same sample, preferably markers of a plurality of different organisms, preferably using a single extraction protocol. Thus, instead of processing separate samples by different extraction methods to test for two or more markers, the same sample can be processed using a single extraction protocol. The methods thus allow for patient samples to be processed with higher speed and efficiency than previously achieved. The methods are also more amenable to use in rapid point of care assay devices, especially in cartridge, microfluidic or biochip based approaches to multianalyte measurements; the use of a single extraction procedure allowing for a significant reduction in the complexity of the sample preparation that must be carried out by the user or the instrumentation.

Moreover, the extraction methods of the preferred embodiments of the present invention work efficiently with a wide variety of markers, including proteinaceous, carbohydrate, nucleic acid and/or lipid markers, from a wide variety of microorganisms. The marker may be a non-carbohydrate marker (e.g., an antigen bound by an antibody which recognizes an epitope that is not comprised of a carbohydrate moiety).

One embodiment of the invention is a method for measuring a plurality of different organisms in a sample. Measurement includes detecting the presence or absence of a marker indicative of an organism, quantitating the amount of marker, identifying a known marker, determining the identity of a previously unknown marker, etc. At least one of the organisms is, preferably, a gram positive bacteria, more preferably a *Streptococci* or *Enterococci* bacteria (e.g., Strep Group A, B, F and G bacteria). These bacteria are measured by extracting and measuring a marker from said bacteria, preferably a cell wall-associated antigen, more preferably a group specific antigen. Preferably, at least one of the other organisms that is measured is selected from the group consisting of fungi, viruses and gram negative bacteria and/or at least one of the other organisms is measured by measuring a proteinaceous (e.g., an epitope comprised of amino acids which is recognized by an antibody), carbohydrate, nucleic acid and/or lipid marker. Viruses that are measured are preferably selected from the group consisting of Rhinoviruses, Parainfluenza viruses, Influenza type A, B or C viruses, Respiratory syncytial viruses (RSV), Coronaviruses, Adenoviruses, Coxsackie A viruses, Herpes simplex viruses, Enteroviruses, Epstein-Barr viruses, Cytomegaloviruses, and Papillomaviruses.

The invention includes methods for extracting one or more markers, preferably two or more markers, comprising contacting a sample (preferably a mucus-containing sample such as a pharyngeal and/or nasal-pharyngeal swab or a nasal wash) with an extraction reagent comprising an oxidizing acid (preferably nitrous acid) and, optionally, a detergent. The marker(s) are, preferably, derived from microorganisms (more preferably selected from pathogenic microorganisms responsible for a disease or condition of the upper respiratory tract). The extracting reagent extracts markers from the sample and makes them accessible for measurement (preferably by immunoassay, more preferably by multiplexed immunoassay, even more preferably with a patterned array of immobilized antibodies directed against markers).

Advantageously, the method may be used to extract protein markers and/or markers from viruses. More advantageously, the method is used to extract at least one protein marker (preferably from a virus) and at least one carbohydrate marker (preferably from a bacteria, more preferably a cell wall marker from a gram-positive bacteria) from the same sample using a single common extraction procedure. The method may also include the step of preparing an extracting reagent, preferably by combining an oxidizing salt (most preferably a nitrite salt) with an acid (preferably hydrochloric acid, sulfuric acid, acetic acid or citric acid).

The invention also includes methods for analyzing a sample for the presence of at least one microorganism or, more preferably, for any one of a plurality of microorganisms of interest. The microorganism(s) are, preferably, selected from pathogenic microorganisms responsible for a disease or condition of the upper respiratory tract. The method comprises contacting a sample (preferably a mucus-containing sample such as a pharyngeal and/or nasal-pharyngeal swab or a nasal wash) with an extraction reagent comprising an oxidizing acid (preferably nitrous acid) and, optionally, a detergent. The extracting reagent extracts markers from the sample matrix and/or the microorganisms of interest and makes them accessible for measurement (preferably by immunoassay, more preferably by multiplexed immunoassay, even more preferably with a patterned array of immobilized antibodies directed against markers). The processed sample is then analyzed to measure extracted markers and thereby to measure the corresponding microorganisms of interest. Advantageously, the method may be used to measure protein markers e.g. markers from viruses. More advantageously, the method measures at least one protein marker (preferably from a virus) and at least one carbohydrate marker (preferably from a bacteria, most preferably a cell wall marker from a gram-positive bacteria) from the same sample using a single common extraction procedure. The method may also include the step of preparing an extracting reagent, preferably by combining an oxidizing salt (most preferably a nitrite salt) with an acid (preferably hydrochloric acid, sulfuric acid, acetic acid or citric acid).

In one specific embodiment of the present invention, measurement can be further improved by using immunoassays with electrochemiluminescent-labeled antibodies (i.e., markers which are antigens recognized by the antibodies). The results may be used in therapeutic monitoring and directed treatment planning.

The invention also relates to extraction reagents comprising an oxidizing acid (preferably nitrous acid) and, preferably, a surfactant. The invention further relates to compositions comprising the extraction reagent and one or more of the following components: (a) sample, (b) assay reagents, (c) labeled reagents, and combinations thereof. The invention still further relates to kits comprising, in one or more containers, vessels or compartments, the extraction reagent (or portions thereof) and, preferably, one or more additional extraction and/or assay components.

In one specific embodiment, the kit also comprises a solid support having an immobilized patterned array of antibodies directed against markers of interest, preferably including a first region containing a first binding reagent directed against a first marker and a second region containing a second binding reagent directed against a second marker. The kit may also contain a base or a pH buffer for neutralizing an extraction reagent.

DETAILED DESCRIPTION OF THE INVENTION

Extraction refers to the processing of a sample so as to make a marker more accessible for measurement. By way of example, extraction includes the liberation and/or solubilization of markers from cells, microorganisms or organelles, e.g., by (i) rupturing or solubilizing membranes, cell walls, envelopes, etc. to release markers comprised or encased within, attached to and/or incorporated into the membranes, cell walls, envelopes, etc., (ii) cleaving a marker from a larger chemical moiety, (iii) breaking down and/or dissolving a polysaccharide coat and/or (iv) breaking down and/or dissolving a jelly coat. Extraction also includes the liberation of markers, cells, organelles and/or microorganisms from components of the surrounding sample matrix. The matrix may include the medium in which the organism or the marker is present. The methods of the invention are especially well adapted to extract markers from sample matrices that comprise mucus.

The extraction methods of the current invention allow for the extraction of one or more markers of different disease conditions or disorders from a single sample using a single extraction protocol in a single reaction volume using an extraction reagent of the present invention, preferably an oxidizing acid, more preferably a nitrous acid, and optionally a surfactant.

The markers suitable for extraction and/or measurement using the present invention include substances (or fragments and/or derivatives thereof) that are characteristic of an organism and/or a class of organisms of interest and that can be used to measure the organism and/or the class of organisms of interest. Microorganism, as used herein, should be understood to include viruses, bacteria, fungi and protozoa. Measured, as used herein, is understood to encompass quantitative and qualitative measurement, and encompasses measurements carried out for a variety of purposes including, but not limited to, detecting the presence of an analyte, quantitating the amount of an analyte, identifying a known analyte, and/or determining the identity of an unknown analyte in a sample.

In one preferred embodiment, the useful markers of the present invention are characteristic of pathogenic microorganisms and/or classes of pathogenic microorganisms that cause disease or a disease condition, preferably respiratory infections or venereal disease, more preferably pharingytis, sinusitis, pneumonia, bronchitis, flu and/or the common cold. Preferred markers include molecules of proteinaceous (e.g., peptides, proteins, toxins and antibiotics), carbohydrate, nucleic acid or lipid nature or combinations thereof (e.g., glycoproteins). The most preferred markers of the present invention are proteins, peptides, and polysaccharides. At least one of the plurality of markers is preferably proteinaceous.

Among specific examples of the markers suitable for extraction and/or measurement using the present invention are (a) cell wall polysaccharides of gram positive bacteria such as the group specific antigens of Streptococci Groups A, B, F, G (these streptococci antigens comprised primarily of N-acetyl-glucosamine and rhamnose can be used to identify and discriminate between Streptococci Groups A, B, F, G); (b) lipoteichoic acids (these bacterial glycolipid antigens can be used to identify Enterococci Group D); (c) Influenza specific proteins such as influenza nucleoprotein, matrix protein, hemagglutinin, neuraminidase and/or peptide derivatives thereof which can identify influenza, preferably the influenza A and/or B nucleoprotein and/or peptide derivatives thereof, and (d) respiratory syncytial virus (RSV) specific proteins which can be used to identify RSV such as the G, F, matrix, nucleoprotein and/or peptide derivatives thereof, preferably the G or F proteins and/or peptide derivatives thereof. Another class of preferred markers includes bacterial toxins (e.g., macrocyclic toxins).

The present invention has been developed for use with complex biological matrices such as complex viscous biological fluids containing multiple types of biological and small organic molecules, for example mucous exudates rich in protein matter. Surprisingly, the extraction procedures of the present invention reduce the non-specific binding that can be associated with a matrix in the sample and simultaneously lower the matrix viscosity by solubilizinc and/or breaking down viscous or solid components of the sample matrix by using the extraction reagent of a present invention, preferably an oxidizing acid, more preferably a nitrous acid, and optionally a surfactant.

Preferred embodiments of the invention use a simple one-step or two-step sample preparation protocol that liberates markers from organisms and/or breaks down and/or liquefies biological matrices. Biological matrices that may be analyzed using the methods of the invention include environmental samples (e.g., water, food, sludges filtered from water or air, environmental wipes, etc.), serum, plasma, blood, synovial fluid, cerebrospinal fluid, sebaceous discharges, pus, mucous membrane secretions, lavage, etc. Most preferably, the samples are mucus-containing samples such as nasal secretions, sputum, phlegm, pharyngeal exudates, urethral or vaginal secretions, and washes of such membrane surfaces. In one preferred embodiment of the invention, the extraction protocol simultaneously liberates two or more markers, preferably of carbohydrate and/or proteinaceous nature, simultaneously from one or more different organisms in the same sample. Advantageously, the methods of the invention may be used to simultaneously extract different classes of markers and, e.g., may be used to extract a protein antigen from one organism and a carbohydrate antigen from a different organism (preferably, a carbohydrate cell wall antigen from a gram positive bacteria). This preferred embodiment is especially advantageous where there is a composite disease condition which results from a combination of different organisms and the patient is in need of treatment with a combination of medications. According to another preferred embodiment, if the diagnosis cannot be determined from the clinical presentation of the disease, a multianalyte test can be performed to identify the infectious organism(s).

The organisms of interest in the present invention are selected from the groups of bacteria, viruses, and fungi. The infectious microorganisms that cause pathology and are of particular interest in the present invention include, but are not limited to:

a) bacterial strains, such as bacterial strains of GABHS (Strep A), *Arcanobacterium haemolyticum, Bacteroides fragilis, Enterococcus, Haemophilus influenza, Haemophilus dtcreyi, Streptococcus pneumoniae, Streptococcus pyogenes, Staphylococcus aurells, Moraxella (Branhamella) catarrhalis, Parainfluenza, Treponema pallidum, Bordetella pertussis, Corynebacterium diphtheriae, Calymmatobacteriumi, Actinomyces, Bacteroides, Fusobacterium, Clostridium, Mobiluncus, Pseudomonas, Nocardia, Legionella pneumophila, Chlamydia trachomatis, Chlamydia pneumoniae, Chlamydia psittaci, Neisseria gonorrheae, Ureaplasma urealyticum, Gardnerella vaginalis, Mycoplasma pneumoniae, Klebsiella pneumoniae, E. coli*, and *Mycobacterium tuberculosis;* b) viral strains, such as viral strains of Rhinovirus, Parainfluenza virus, Influenza type A, B or C virus, Respiratory syncytial virus (RSV), Coronavirus, Adenoviruses, Coxsackie A virus, Herpes simplex virus, Enterovirus, Epstein-Barr virus, Cytomegalovirus, or Papillomavirus; and c) fungi, such as *Candida* spp., *Candida albicans, Pneumocystis carinii, Histoplasma, Blastomyces, Coccidioides*, or *Cryptococcus* d) protozoa, such as *Cryptosporidium parvum, Cyclospora cayetanensis, Entamoeba histolytica*, or *Giardia lamblia.*

Surprisingly, the methods and kits of the present invention can be used to process a wide variety of samples. Preferably, the sample is a biological sample, more preferably a clinical sample that contains pathogenic organisms. The sample may be collected by swabbing or washing a mucous membrane or by removing fluid secreted from a mucous membrane. According to a preferred embodiment, the sample is collected from a patient using a sampler (e.g., aspirator, swab, suction, or scrape), preferably by a swab (e.g., a nasal, nasal-pharyngeal, pharyngeal or genital swab) or a wash (e.g., a nasal or pharyngeal wash). In another specific embodiment, the sample is concentrated or cultured to increase the cellular or viral particle count. The sample is then subjected to the extraction protocol using an extraction reagent, preferably an oxidizing acid, more preferably a nitrous acid, and optionally a surfactant according to the present invention.

The extracted markers are also preferably subsequently measured using any of a number of techniques available to the person of ordinary skill in the art, e.g., immunoassays and immunochromatographic assays. One preferred embodiment of the invention measures multiple markers of interest in a sample using a multiplexed assay format, preferably a multiplexed immunoassay format, most preferably using a patterned array of immobilized antibodies directed against the markers.

Thus, one broad aspect of the invention relates to methods of treating one or more samples suspected to contain one or more markers to prepare such samples for analysis. Preferably, the sample (preferably a biological sample, more preferably a clinical sample) is brought into contact with the extraction reagent of the present invention, preferably an oxidizing acid, more preferably a nitrous acid, and optionally a surfactant, for a period of time sufficient to extract the markers of interest. At the same time, the markers may be dissociated from each other, optionally after pH neutralization and/or dilution. Combined extraction and dissociation of markers in the sample allows multiplex analysis of separate markers or simplified processing when separately analyzed. Preferably, the methods further comprise the step of analyzing the treated samples.

According to one preferred embodiment, the sample is a single biological sample, more preferably a clinical sample, even more preferably from a single sample from a single patient in a single volume. According to another preferred embodiment, the method extracts one or more markers from a series of samples from a series of patients, each sample being processed in a different single volume.

One embodiment relates to a method for extracting one or more markers, preferably two or more markers, more preferably three or more markers, even more preferably five or more markers and most preferably at least ten or more markers from a sample using the extraction reagent of the present invention, preferably an oxidizing acid, more preferably a nitrous acid, and optionally a surfactant. Preferably, at least one of the markers is of proteinaceous, nucleic acid, or lipidic nature (e.g., an epitope which does not contain a carbohydrate component and is recognized by a binding reagent). According to another embodiment, at least one of the markers is a viral or fungal marker.

Another embodiment includes simultaneously extracting more than one marker in a single volume from a single sample containing a complex biological matrix. More specifically, using a simple fast procedure utilizing the extraction reagent of the present invention, preferably an oxidizing acid, more preferably a nitrous acid, and optionally a surfactant, a single sample may be processed to extract and measure markers associated with a variety of different organisms, preferably a panel of pathogenic microorganisms, most preferably a panel of pathogenic microorganisms associated with upper respiratory tract infections. The timely identification of the pathogenic microorganisms responsible for a disorder or disease condition (e.g., colds, pharyngitis, tracheobronchitis, croup, sinusitis, bronchiolitis, pneumonia, etc.), for example, will lead to improved patient care and treatment. Accordingly, in one embodiment of the present invention, the extraction protocol successfully extracts (and preferably also separates) multiple markers. Preferably, the markers are organism markers, more preferably markers from different organisms, and even more preferably bacterial, viral and/or fungal markers.

According to one preferred embodiment, the chemical extraction not only extracts an antigen from a microorganism but also simultaneously liquefies or decreases the viscosity of a sample or a matrix of a sample, preferably, a matrix of a mucous excretion (exudate) using the extraction reagent of the present invention, preferably an oxidizing acid, more preferably a nitrous acid, and optionally a surfactant.

Yet another embodiment relates to methods for measuring two or more markers, preferably organism markers, preferably different organism markers, more preferably bacterial, viral and/or fungal markers, by contacting a sample containing one or more organisms (preferably two or more organisms) with the extraction reagent, preferably an oxidizing acid, more preferably a nitrous acid and optionally a surfactant. Preferably, the methods include separating two or more markers from a matrix, thereby preparing an assay composition, preferably also neutralizing the pH of the assay composition (e.g., adding base and/or buffer to obtain a pH of between 6.0 and 8.5); and detecting or measuring the two or more markers within said assay composition, preferably in a single volume, or, alternatively, in two or more detection volumes containing portions of the same sample.

The extraction methods of the invention may include preconcentrating a sample, preferably by filtration or centrifugation, prior to contacting the sample with an extraction reagent and/or prior to the measurement. Also, centrifugation or filtration can be used to remove particulate debris left after solubilization, preferably before measuring of solubilized markers.

According to one specific embodiment of the invention, the measurement method is a diagnostic test for patients suspected of having an infectious disease or condition, preferably an infectious disease, a condition of an upper respiratory tract, and/or a venereal disease.

According to yet another preferred embodiment, the method includes measuring the marker(s). The extraction protocols of the present invention result in an assay composition that is suitable for analysis by a variety of diagnostic assay formats including many assay formats known in the art for the detection of one or more microorganism markers.

According to another embodiment of the invention, the methods of the invention preferably further comprise the step of measuring markers in a sample. In one specific embodiment, the present invention provides a method for measuring one or more, preferably two or more markers in a sample, wherein at least one of the markers is a proteinaceous, carbohydrate, nucleic acid, lipid molecule or combinations thereof. According to another embodiment, the present invention provides a method for measuring one or more, preferably two or more markers in a sample, wherein at least one of the markers is a viral, bacterial or fungal marker. Preferably, two or markers are measured in the same sample through the use of a multiplexed measurement.

One embodiment of the invention is a method for measuring a plurality of different organisms in a sample. At least one of the organisms is, preferably, a gram positive bacterium, more preferably a *Streptococci* or *Enterococci* bacteria (e.g., Strep Group A, B, F and G bacteria). This bacterium is measured by extracting and measuring a marker from said bacteria, preferably a cell wall-associated antigen, more preferably a group specific antigen. Preferably, at least one of the other organisms that is measured is selected from the group consisting of fungi, viruses and gram negative bacteria and/or at least one of the other organisms is measured by measuring a proteinaceous, carbohydrate, nucleic acid and/or lipid marker. Viruses that are measured are preferably selected from the group consisting of Rhinovirus, Parainfluenza virus, Influenza type A, B or C virus, Respiratory syncytial virus (RSV), Coronavirus, Adenovirus, Coxsackie A virus, Herpes simplex virus (HSV), Enterovirus, Epstein-Barr virus, Cytomegalovirus, and Papillomavirus.

There are a variety of methods available for measuring microorganisms or markers associated with microorganisms subsequent to the extraction step. These techniques include, but are not limited to, cell culture-based assays, agglutination tests, immunoassays (or other assay formats based on the use of specific binding partners of the analyte of interest), immunochromatographic assays, enzymatic assays, etc. Some techniques allow for measurements to be made by visual inspection, others may require or benefit from the use of an instrument to conduct the measurement. A large number of detection techniques are available for analyzing the products of binding assays. These include solid phase binding assay techniques in which binding reaction products are formed on a surface and homogenous binding assay techniques in which binding reaction products remain in solution. Techniques may detect binding events by measuring the participation of labeled binding reagents (e.g., via fluorescence, chemiluminescence, radioactivity, magnetic, enzymatic activity measurements of labels having these properties) or may not require the use of labels (e.g., techniques based on measuring changes in mass or refractive index such as surface acoustic wave and surface plasmon resonance measurements). In addition, there are chemical tests, where certain analytes cause a color change when exposed to certain chemicals. Other suitable detection methods include the use of enzymatic biosensors where an enzyme recognizes a certain analyte, catalyzes chemical conversion of an analyte to one or more reaction products and the reaction products are detected by eye, or by instrument.

Additional examples of techniques that can be used for measuring include mass spectrometry, chromatography, electrophoresis, agglutination, western blot, specific binding assays, immunoassay, immunofluorescence and immunochromatographic assays. The preferred method of the present invention is the specific binding assay, preferably immunoassay, or immunochromatographic assays.

The immunoassay or specific binding assay according to the preferred embodiments of the invention can involve a number of formats available in the art. The antibodies and/or specific binding partners can be labeled with a label or immobilized on a surface. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.*, 67 (Suppl 1); 51-64 (1966) and Hochman, J. Inbar, D. and Givol, *D. Biochemistry* 12: 1130 (1973), hereby incorporated by reference). The term also includes intact antibody molecules, antibody fragments and antibody constructs that have been chemically modified, e.g., by the introduction of a label.

Preferably, the detection method is a binding assay, more preferably an immunoassay, and the detection is performed by contacting an assay composition with one or more detection molecules capable of specifically binding with the marker(s) of interest. More preferably, the assay uses a sandwich or competitive binding assays format. Examples of sandwich immunoassays performed on test strips are described in U.S. Pat. No. 4,168,146 to Grubb et al. and U.S. Pat. No. 4,366,241 to Tom et al., both of which are incorporated herein by reference. Examples of competitive immunoassay devices suitable for use with the present invention include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference. Most preferably, at least one of the binding reagents employed in such an assay is immobilized on a solid phase support.

According to a preferred embodiment of the invention, samples are subjected to the extraction method of the invention followed by measurement of marker(s) using electrochemiluminescence-based assay formats, most preferably electrochemiluminescence (ECL) based immunoassays. The high sensitivity, broad dynamic range and selectivity of ECL are important factors for medical diagnostics. Commercially available ECL instruments have demonstrated exceptional performance. They have become widely used for reasons including their excellent sensitivity, dynamic range, precision, and tolerance of complex sample matrices.

Preferably, the marker is measured in a solid phase sandwich immunoassay, most preferably, employing ECL detection. In a solid phase sandwich immunoassay, two antibodies directed against the marker are used: i) a capture antibody that is linked or capable of being linked (e.g., through the formation of a specific binding pair such as a biotin-streptavidin interaction) to a solid phase and ii) a detection antibody that is linked or capable of being linked (e.g., through the formation of a specific binding pair such as a biotin-streptavidin interaction) to a label, preferably an ECL label. A sample comprising the solublilized marker is contacted with the two antibodies and the solid phase so that in the presence of the marker the two antibodies bind to the marker to form a "sandwich complex" on the solid phase comprising the label. The label on the solid phase is measured so as to measure the marker in the sample.

Certain commercially available instrumentation uses flow cell-based designs with permanent reusable flow cells. Most binding assays carried out on these types of instruments use magnetically responsive particles as a solid phase support for a solid phase binding assay. Immunocomplexes comprising ECL labels that are bound to the particles are collected on an electrode in the flow cell with the aid of a magnet. The labels on the collected particles are induced to emit ECL by application of a voltage to the electrode and the ECL is measured to measure the amount of label. The ECL assay method may also comprise the step of introducing an ECL coreactant prior to application of the ECL inducing voltage.

Recently, ECL instrumentation has been disclosed that uses reagents immobilized on an electrode used to induce ECL (see, e.g., U.S. Pat. Nos. 6,140,045; 6,066,448; 6,090,545; 6,207,369 and Published PCT Appl. No. WO98/12539). In this case, the electrode itself is the solid phase support. Multi-well plates having integrated electrodes suitable for such ECL measurements have also been recently disclosed (see, e.g., copending U.S. application. Ser. Nos. 10/185,274 and 10/185,363 entitled "Assay Plates, Reader Systems and Methods for Luminescence Test Measurements", each filed on Jun. 28, 2002, hereby incorporated by reference). These multi-well plates having integrated electrodes include plates having multiple assay domains within a well wherein multiple binding reagents could be immobilized. The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates).

According to the present invention, electrochemiluminescence measurements are preferably carried out using screen-printed carbon ink electrodes, such as carbon ink electrodes patterned on the bottom of specially designed cartridges or multi-well plates (e.g., 24-, 96-, 384-etc. well plates). Electrochemiluminescence from ECL labels on the surface of the carbon electrodes is induced and measured using an imaging plate reader as described in copending U.S. application. Ser. Nos. 10/185,274 and 10/185,363 (both entitled "Assay Plates, Reader Systems and Methods for Luminescence Test Measurements", filed on Jun. 28, 2002, hereby incorporated by reference). Analogous plates and plate readers are now commercially available (Sector HTS instrument, Meso Scale Discovery).

Thus, to further improve the sensitivity and selectivity of the measurement or other analysis of the organism(s) of interest, preferred embodiments of the present invention employ electrochemiluminescent (ECL) labels in immunoassays and labeled reagents, preferably antibodies that are labeled with ECL labels. At this time, there are a number of commercially available ECL labels for analytical measurements. Examples of electrochemiluminescent labels, co-reagents and detection or measuring methods and systems are described in U.S. Pat. Nos. 5,093,268; 5,147,806; 5,324,457; 5,591,581; 5,597,910;

5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369 and 5,589,136 and Published PCT Nos. WO99/63347; WO00/03233; WO99/58962; WO99/32662; WO99/14599; WO98/12539; WO97/36931; WO98/57154; and PCT/US02/19788, all of which are incorporated hereby by reference. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863, herein incorporated by reference). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody and the participation of the binding reagent in a binding interaction can be monitored by measuring ECL emitted from the ECL label.

One embodiment of the invention relates to a method of measuring one or more markers (preferably two or more markers) comprising:
(a) contacting a sample containing one or more markers with an extraction reagent of the invention thereby forming a composition containing one or more extracted markers;
(b) contacting said composition with a reagent comprising one or more binding reagents capable of binding with said one or more extracted markers, said binding reagents being linked to ECL labels;
(c) inducing said labels to induce electrochemiluminescence; and
(d) measuring the emitted electrochemiluminescence.

One embodiment of the invention relates to a method of measuring a plurality of different organism types in a sample comprising:
(a) contacting said sample with an extraction reagent comprising nitrous acid, thereby forming an assay composition; and
(b) measuring, in said assay composition, markers of said plurality of organism species so as to measure said plurality of organisms species.

Preferably, the reagents further comprise one or more capture reagents capable of binding with said one or more extracted markers, wherein the capture reagents are attached to beads or attached to a solid support (e.g., a working electrode for inducing electrochemiluminescence).

Preferably, the method further comprises adjusting or neutralizing the pH of the composition after step (a).

Preferably, the reagent comprises a plurality of different binding reagents capable of binding a plurality of different markers and, optionally, a plurality of different capture reagents.

Another preferred embodiment of the present invention relates to a clinical method for the simultaneous extraction of a variety of microorganism markers (preferably markers of different and/or diverse chemical nature (e.g., proteins, carbohydrates, etc.) from one or more patients with diseases of the upper respiratory tract. The sample is taken from a patient, preferably from a patient with an upper respiratory tract condition, preferably by a throat swab or nasal wash. The sample is brought in contact with the extraction reagent of the present invention, preferably an oxidizing acid, more preferably a nitrous acid, and optionally a surfactant, which liberates microorganism markers and advantageously liquefies mucous exudates to form an assay composition. The resulting assay composition is either tested directly for the presence of the microorganisms of interest or neutralized with a pH buffer and then tested. Preferably, the microorganisms of interest are Strep A, Flu A/B and RSV. The sample processing and testing may be advantageously performed "in the office", preferably while the patient is at the physician's office. One of the main advantages of the present invention is that a single extraction step can be coupled to the measurement of a variety of different microorganisms. The rapid results will help doctors in (i) providing proper and timely treatment planning, (ii) correctly assigning emerging antiviral drugs and (iii) reducing unnecessary use of antibiotics.

Another aspect of the invention relates to extraction reagents for use in the present method. One embodiment relates to an extraction reagent comprising an oxidizing acid. Preferably, the reagent further comprises a surfactant. Surprisingly, the extraction reagents of the present invention are broadly applicable to a variety of microorganisms and matrices.

Another embodiment relates to an extraction reagent consisting essentially of an oxidizing acid, preferably an oxidizing acid and a surfactant in aqueous solution. According to another embodiment, the extraction reagent consists essentially of an oxidizing acid, a surfactant and one or more components selected from the group consisting of: (a) detection label (e.g., ECL label), (b) binding reagents capable of binding with one or more markers, (b) ECL co-reactant(s), and (c) blocking agent (e.g., BSA). The solution may be neutralized by adding base and/or buffer to obtain a pH of between 6.0 and 8.5.

Preferably, the oxidizing acid is a nitrous acid. Nitrous acid has been known in the art to be suitable for exposing the group A antigen of Strep A but was previously considered strongly detrimental to the extraction of protein, nucleic acid, and lipidic markers. The nitrous acid is preferably combined with a surfactant such as a non-ionic detergent to further improve the efficiency of the extraction.

In one preferred embodiment of the invention, the nitrous acid used is prepared by combining nitrite salt with an acid. Useful nitrites include both inorganic nitrites such as sodium, potassium, lithium nitrites and organic nitrites. Preferably, the nitrite salt is sodium nitrite. Useful acids include both inorganic acids such as hydrochloric and sulfuric acids and organic acids such as acetic and citric acids. Preferably, the acid is an organic acid, more preferably acetic acid.

Suitable surfactants for use with the extraction reagent of the invention include, but are not limited to, Tween, TRITON, CYMAL, ZWITTERGENT, IPTG, CHAPS, CHAPSO, Anapoe, BAM, FOS-Choline, Pluronics, Tetronics, Brij, Span, HEGA, C-HEGA, n-Do(Tri, Tetra, Hexa, Un)decyl-β-D-maltoside and L-, D-DAO families of surfactants.

According to one preferred embodiment, the extraction reagent is produced by combining a nitrite salt such as sodium nitrite with an acid and optionally a surfactant. Preferably, the extraction reagent is produced by combining equal volumes of sodium nitrite solution and acetic acid and optionally each component (or either component) containing a surfactant, preferably Tween-20. More preferably; combining from 0.5 M to 10M sodium nitrite solution with a matching concentration of an acid (preferably acetic acid) ranging from 0.1 M to 0.5M and optionally each solution containing from 0.5% to 5% surfactant (preferably Tween-20) (or either solution containing twice that amount), most preferably combining from 2 M to 7.5M sodium nitrite solution with from 0.125 M to 0.188M acid (preferably acetic acid) and optionally each solution containing from 1 to 3% surfactant (preferably Tween-20).

Concentrated extraction reagents can also be used according to the present invention. Higher reagent concentration results in a more rapid extraction while lower extraction reagent concentration might be preferred because it makes the neutralization process easier, minimizes protein denaturation and denitrification, as well as preserving marker antigenicity and reagent stability. In one specific embodiment, for example, a 2M sodium nitrite, 1% Tween-20 solution is combined with 0.125 M acetic acid, 1% Tween-20 solution. In another specific embodiment, a 7.5M sodium nitrite, 3% Tween-20 solution is combined with 0.188 M acetic acid and 3% Tween-20 solution.

In one preferred embodiment of the invention, one of the two reagents combined to produce the nitrous acid is used in dry form, preferably a dry form of an organic acid or a dry form of any nitrite salt.

Another aspect of the invention relates to improved compositions for extracting and, preferably, measuring markers from a sample such as a complex biological matrix.

One embodiment relates to a composition which contains: (a) two or more markers (preferably two or more extracted markers), preferably organism markers, preferably microorganism markers, preferably markers from different organisms, more preferably bacterial, viral and/or fungal markers, and (b) an oxidizing acid, preferably an oxidizing acid and a surfactant having, preferably a non-ionic surfactant, the composition having pH range from 2 to 5, preferably having pH neutralized prior to detection. Preferably, the composition is an assay composition which can be used for rapid diagnosis of multiple infectious microorganisms that cause disease.

Yet another embodiment of the present invention is directed to a composition containing one or more extracted markers, preferably organism markers, preferably microorganism markers, preferably different organism markers, more preferably bacterial, viral or fungal markers, and an oxidizing acid having pH range from 2 to 5, preferably an oxidizing acid and a surfactant, preferably a non-ionic surfactant, preferably having pH neutralized prior to measurement, and at least one marker is a protein, peptide, toxin, nucleic acid or lipid, or at least one marker is a viral or fungal marker. Preferably, the assay compositions may also comprise one or more detection molecules or capture molecules (i.e., binding reagents) capable of specifically binding with the marker(s) of interest, detection labels, and/or co-reactants, etc.

In one embodiment, the assay composition comprises a sample and an extraction reagent, wherein a sample comprises organisms, toxins, and/or viral particles and an extraction reagent according to the present invention. In one preferred embodiment, the assay composition may further comprise a pH buffer or base, which can neutralize the extraction reagent. For example, a neutralizing buffer (preferably Tris or PBS, more preferably 1M to 2 M Tris) is added to a biological sample after the sample has been incubated with the extraction reagent for a sufficient period of time. The final pH of the assay composition is preferably neutral, preferably the pH is from 6.0 to pH 8.5. In one specific embodiment of the present invention a neutralizing buffer can be added in a dry form.

Another aspect of the invention relates to kits for extracting one or more (preferably two or more) markers from a sample using the extraction method of the instant invention, and preferably for measuring the markers.

The invention also relates to a kit for measuring a plurality of different organism types in a sample comprising, in one or more containers: (a) an acid, (b) a nitrite salt, (c) a surfactant, (d) a first binding reagent that binds a first marker from a first organism of said plurality of different organism types, and (e) a second binding reagent that binds a second marker from a second organism of said plurality of different organism types. Preferably the first and second binding reagents are antibodies.

The kit will preferably include, in one or more containers, the extraction reagents, preferably nitrous acid, and, optionally, a surfactant. Preferably, the kit further includes one or more assay components. More preferably, the kits include nitrous salt, an acid and a non-ionic surfactant, in separate containers or compartments to allow for rapid recombination to produce the extraction reagent of the present invention.

The invention is also directed to a kit for extracting two or more markers from a sample, preferably organism markers, preferably microorganism markers, preferably different organism markers, more preferably bacterial, viral or fungal markers, for use in one or more assays comprising, in one or more containers, vessels or compartments: (a) an acid, (b) a nitrite salt, (c) a surfactant, preferably a non-ionic surfactant and (d) at least one extraction component selected from the group consisting of: (i) a pH buffer/pH neutralizer, (ii) a sampling device (e.g., swab, aspirator, swab, suction, or scrape), (iii) preservatives, (iv) stabilizing agents, (v) extraction vessel, (vi) bleach, (vii) desiccants, (viii) capture moiety, and (ix) detection moiety.

Another embodiment the invention relates to a kit for extracting one or more markers from a sample, preferably organism markers, preferably microorganism markers, preferably different organism markers, more preferably bacterial, viral or fungal markers, for use in one or more assays comprising, in one or more containers: (a) an acid, (b) a nitrite salt, (c) a surfactant, preferably a non-ionic surfactant and (d) at least one extraction component selected from the group consisting of: (i) a pH buffer/pH neutralizer; (ii) a sampling device (e.g., aspirator, swab, suction, or scrape); (iii) preservatives, (iv) stabilizing agents, (v) extraction vessel, (vi) bleach, (vii) desiccants, (viii) capture moiety, and (ix) detection moiety, where at least one marker is a protein, peptide, toxin, nucleic acid or lipid, or at least one marker is a viral or fungal marker. The kits of the present invention may further comprise one or more binding reagents capable of binding the markers of interest. The kits may also supply a nitrite salt in dry or solution form and an acid in dry or solution form to be combined to form a nitrous acid and a Tris base or buffer or PBS as a pH buffer/pH neutralizer.

Preferably, the kit further comprises a sampling device (e.g., aspirator, swab, suction, scrape, etc.), extraction vessel(s), pH buffer(s), preservative(s), stabilizer(s), desiccant(s), and bleach.

The kit is preferably configured for use or compatible with a variety of detection methods, e.g., immunoassay, immunochromatographic assay, specific binding assay, chromatographic and mass spectroscopic assays and is not limited to a specific detection technique.

Alternatively, according to one preferred embodiment, the kit further includes specific binding partners, preferably labeled specific binding partners, more preferably ECL labeled specific binding partners. The binding partners of the kits of the present invention may include a variety of substances including, but not limited to antibodies, peptide or nonpeptide mimetics, lectins, antigens, DNA and/or RNA aptamers, biotin, streptavidin, avidin, haptens, antihaptens, antibiotics, etc.

In one preferred embodiment, the kit comprises two binding partners where the first partner is immobilized on a solid support such as a multi-well plate bottom or a bead and the second partner is labeled with a label, preferably an ECL label. Examples of the ECL detection kits include those available from IGEN International, Inc. (Gaithersburg, Md.), Meso Scale Diagnostics (Gaithersburg, Md.), and Roche Diagnostics. Such kits can be combined with the extraction reagents of the invention. Other suitable kits are described in the above-described electrochemiluminescence patents, hereby incorporated by reference.

In one preferred embodiment, a solid support has a patterned array of binding reagents (preferably, antibodies) immobilized thereon so as to form at least a first region having a first binding reagent and a second region having a second binding reagent. These binding reagents, preferably, are directed to markers of interest such as markers for organisms of interest.

According to preferred embodiments of the present invention, the kit comprises a pre-assembled system or device, e.g., a cartridge or multi-well plate, containing one or more of the necessary reagents including the extraction reagent of the present invention, preferably stored in one or more compartments. Such a kit would allow for rapid "in the office" marker extraction and subsequent analysis.

The invention is further illustrated by the following examples.

EXAMPLES

The following examples are illustrative of some of the extractions, plates, kits and methods falling within the scope of the present invention. They are, of course, not to be considered in any way limitative of the invention. Numerous changes and modifications can be made with respect to the invention by one of ordinary skill in the art without undue experimentation.

Materials and Methods:
Extraction Reagent:

The extraction reagent was prepared fresh prior to use by mixing equal volumes of a stock sodium nitrite solution (2M sodium nitrite, 1% Tween-20) and a stock acetic acid solution (0.125M acetic acid, 1% Tween-20) to yield a final concentration of 1 M sodium nitrite, 0.5% Tween-20, 0.0625M acetic acid.

In some experiments, a more concentrated extraction reagent was used. This reagent was prepared fresh prior to use by mixing equal volumes of a stock sodium nitrite solution (7.5M sodium nitrite), a stock acetic acid solution (0.188M acetic acid), and a stock solution of 3% Tween. The high concentration extraction reagents were used where specifically indicated.

Bacterial and Viral Preparation:

*Streptococcus pyogenes* (Strep A, ATCC 12385) was grown in trypticase soy broth under 5% $CO_2$ atmosphere at 37° C. until cloudy. This stock was diluted 1:10 with PBS (100 mM phosphate buffer, 150 mM NaCl, pH 7.5).

The viral samples of influenza A, influenza B, and respiratory syncytial viruses ($2.25 \times 10^{12}$ virus particles/ml) were purchased from Advanced Biotechnologies Inc. and diluted to a desired concentration with PBS prior to use.

Mucous Preparation:

Human bronchial mucous samples or nasal discharge samples were obtained from individuals without upper respiratory disease symptoms. A highly viscous sample and a low-viscosity sample were sonicated until a uniform solution was reached.

ECL Label:

The label Compound 1 pictured below (Sulfo-TAG™ NHS Ester, Meso Scale Discovery, a division of Meso Scale Diagnostics, LLC, Gaithersburg, Md.) was used to label biomolecules for electrochemiluminescence measurement.

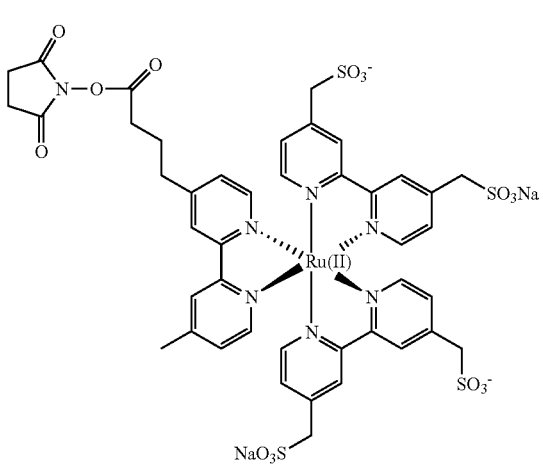

Labeling of biomolecules was carried out by adding the Sulfo-TAG NHS Ester to a solution of the biomolecule in phosphate buffered saline, pH 8.0. The labeled biomolecules were typically purified from unbound label by size exclusion chromatography (e.g., using Superdex Peptide Gel or Sephadex G50, Pharmacia Biosciences) or by reverse phase HPLC. For labeled proteins, the ratio of labels per protein was calculated from the concentration of labels (calculated from the extinction coefficient of Sulfo-TAG label at 455 nM, $\epsilon_{455}$~15, 400 $M^{-1}$ $cm^{-1}$) and the concentration of protein (determined using the BCA Protein Assay, Pierce Chemicals). Polyclonal anti-Strep A antibodies and monoclonal anti-Influenza A, anti-Influenza B, anti-RSV were purchased from Virostat Inc., Fitzgerald Industries International, Research Diagnostics Inc., and Accurate Chemical and Scientific Corp., respectively.

Multi-Well Plates:

Electrochemiluminescence measurements were carried out using specially designed 96-well multi-well plates (Multi-Array™ or Multi-Spot™ plates, Meso Scale Discovery, a division of Meso Scale Diagnostics, LLC, Gaithersburg, Md.).

Measurement Instrument:

Electrochemiluminescence was induced and measured using a Sector HTS™ reader or a Sector PR™ reader (Meso Scale Discovery, a division of Meso Scale Diagnostics, LLC, Gaithersburg, Md.).

Example 1

Detection and Quantification of *S. Pyogenes*

*Streptococcus pyogenes* (Strep A) was diluted with mucous solutions (1:4 volume ratio), mixed, and incubated for 2 hours at room temperature.

The Strep A solutions in mucus (50 ul) were combined with 450 ul of either extraction reagent or one of two control solutions (4% Tween-20 solution in PBS or surfactant-free PBS). After mixing and incubating for 15 minutes, the solutions were combined with and equal volume of phosphate buffered saline (PBS) containing 150 mM phosphate to neutralize the acidity of the extraction reagent. PBS that was free of Strep A was used as a negative control to measure assay background.

A polyclonal anti-strep antibody (to the group A carbohydrate) was immobilized by passive adsorption on screen-printed carbon ink electrodes patterned on the bottom of the specially designed 96-well multi-well plates (High Bind Multi-Array plates, MSD) by depositing 2.5 ul of 50 mg/ml solution of antibody in PBS directly on the electrode surface. After the solution had dried, 250 ul of 5% BSA (bovine serum albumin, Seracare Inc.) in PBS solution was added to each well, and the plate was stored at 4° C. overnight before use. The plate was then washed twice with 300 ul of PBS per well immediately before use. Strep A antigen was measured in the plate via ECL immunoassay. In separate wells of the plate, 25 ul of processed sample was added along with 25 ul of conjugate anti-Strep A antibody labeled with Sulfo-TAG (3 ug/ml). The plate was incubated for 1 hour, washed, filled with ECL Assay Buffer (125 mM tripropylamine in 200 mM phosphate buffer, pH 7.5), and the amount of Strep A antigen was quantified using ECL.

The data (Table I) indicate that the presence of mucus completely inhibits the immunoassay unless the sample is treated with nitrous acid or surfactant and that the former treatment allows for improved Strep A quantification.

TABLE I

| Sample Treatment | Strep A Dilution | ECL from low-viscous mucous sample | ECL from highly viscous mucous sample |
|---|---|---|---|
| Nitrous Acid/1% Tween | 1:1400 | 18500 | 11300 |
| 4% Tween | 1:1400 | 4440 | 3100 |
| None (PBS) | 1:1400 | 2470 | 1780 |
| None (PBS) | No Strep | 2440 | 1720 |

Example 2

Detection and Quantification of Influenza A

Purified influenza A virus ($2.25 \times 10^{12}$ virus particles/ml, Advanced Biotechnologies Inc.) was diluted 1:10 with PBS. This preparation was then diluted with the low-viscosity mucous preparation (1:4), mixed, and allowed to incubate for 2 hours at room temperature.

The influenza solution in mucus (50 ul) was combined with 450 ul of the extraction reagent or one of two control solutions (4% Tween-20 in PBS or surfactant-free PBS). After mixing and incubating for 15 minutes, the solutions were combined with an equal volume of PBS to neutralize the acidity of the extraction reagent. PBS that was free of Flu A was used as a negative control to measure assay background.

A monoclonal anti-Influenza A antibody was immobilized by passive adsorption on screen-printed carbon ink electrodes patterned on the bottom of the specially designed 96-well plates (High Bind Multi-Array Plates, MSD) by depositing 2.5 ul of 50 ug/ml antibody solution in PBS. After the solution had dried, 250 ul of 5% BSA in PBS solution was added to each well, and the plate was stored at 4° C. overnight before use. The plate was washed twice with 300 ul of PBS per well before use. Flu A antigen was measured in the plate via ECL immunoassay. To each well, 25 ul of extracted mucus/antigen solution or PBS was added along with 25 ul of conjugate monoclonal anti-Influenza A antibody labeled with TAG (3 ug/ml). The plate was incubated for 1 hour, washed, filled with Assay Buffer, and the amount of influenza A antigen was quantified using ECL.

The data (Table II) indicate that the presence of mucus inhibits quantification of a viral analyte, unless the sample is treated with a surfactant. Moreover, surprisingly, the nitrous acid treatment does not adversely affect the assay.

TABLE II

| Sample Treatment | Influenza A concentration (vp/ml) | ECL from mucus/influenza A sample |
|---|---|---|
| Nitrous Acid/1% Tween | $1.41 \times 10^9$ | 29600 |
| 4% Tween | $1.41 \times 10^9$ | 25800 |
| None (PBS) | $1.41 \times 10^9$ | 288 |
| None (PBS) | No Flu A | 312 |

Example 3

Simultaneous Detection and Quantification of Multiple Analytes

Solutions of Influenza A, Influenza B, and Respiratory syncytial viruses (Advanced Biotechnologies, Inc.) were prepared in PBS by dilution of purified stock solutions. A 1:100 dilution of a turbid *S. pyogenes* solution culture with PBS was also prepared. Each solution (50 ul) was mixed with 450 ul of freshly prepared extraction reagent and incubated for 5 minutes. The solutions were then neutralized with an equal volume of PBS.

A 4-spot 96 well Multi-Spot Plate (Meso Scale Discovery) was prepared such that each well contained 4 separate spots, and an antibody specific to each of the four analytes was immobilized on separate spots. The antibodies were passively immobilized by depositing 250 nl of a 50 ug/ml solution of the antibody in PBS on each spot. After the solution had dried, 250 ul of 5% BSA in PBS solution was added to each well and the plate was stored at 4° C. overnight. The plate was washed twice with 300 ul of PBS per well before use.

Analyte solutions were dispensed into individual wells (25 ul/well) and a solution containing a mixture of four TAG-labeled conjugate antibodies, each specific for one of the analytes, was also added (25 ul, final concentration of each antibody was 1.5 ug/ml). After mixing for one hour, the plate was washed, 200 ul of ECL Assay Buffer (125 mM tripropylamine in 200 mM phosphate buffer, pH 7.5) was added, and the amount of antigen captured on each spot was quantified using ECL (Table III).

The experiment demonstrates that assays for viruses and *S. pyogenes* can be performed using the same acid pretreatment.

TABLE III

| | ECL from Surfaces Containing Specific Antibodies to: | | | |
|---|---|---|---|---|
| Sample | Influenza A | Influenza B | RSV | Strep A |
| Influenza A | 3382 | 31 | 35 | 57 |
| Influenza B | 94 | 1462 | 97 | 108 |
| RSV | 50 | 42 | 11630 | 75 |
| Strep A | 30 | 22 | 32 | 542 |

Example 4

Effects of Nitrous Acid and Surfactant on Mucus

A sample of mucus in the form of a very viscous nasal discharge was obtained. The sample was divided into two parts (~500 ul each) and placed in clear plastic test tubes. The samples were vortexed, but this had no effect on the samples' physical properties—neither could be poured from the tubes.

To one sample, 200 ul of the extraction reagent (freshly prepared from 1:1 portions of 7.5M sodium nitrite and 0.188M acetic acid) was added. To the other, 200 ul of 20% Tween-20 (w/v) was added. Both samples were briefly vortexed and allowed to incubate for 2 minutes at ambient temperature. No change in the viscosity of the sample treated with surfactant was noted. However, the acid-treated sample had a much lower viscosity, and could be easily poured from the tube. Even greater decrease in the viscosity of the acid-treated mucus was observed after an additional 30 minute incubation.

Example 5

Simultaneous Strep A and Influenza A Detection in a Mucus-Containing Sample

A homogeneous mucous solution was prepared by sonicating a viscous nasal discharge diluted with water. A positive test sample was prepared by mixing the mucous solution with concentrated stock solutions of both Influenza A and Strep A (final dilution 1:500) to simulate a nasal sample obtained from a diseased individual. A negative control sample was prepared by spiking the mucous solution with PBS only. These solutions were placed in an ice bath for 1.5 hours before performing the assay. The high concentration extraction reagent was freshly prepared by adding equal volumes of 0.188 M acetic acid, 3M sodium nitrite, and 3% Tween-20. An extraction reagent lacking surfactant was also prepared by substituting 3% Tween-20 with water.

Each of the positive or negative samples (100 ul) was combined with 450 ul of extraction reagent (with and without surfactant). After a 5 minute incubation, 50 ul of 2M TRIS buffer (pH 7.5) was added to neutralize the solutions. These solutions (75 ul) were combined with a solution containing both anti-Strep A and anti-Influenza A labeled antibodies (10 ul, 25 ug/ml each) and 50 ul of these solutions were added to a MSD 4-spot Multi-Spot Plate containing Strep A and Influenza A capture antibodies pre-adsorbed on different spots, and incubated without mixing for 10 minutes. The plate was then washed, assay buffer was added, and the ECL measured on a Sector HTS™ instrument (Meso Scale Discovery™, a division of Meso Scale Diagnostics, LLC, Gaithersburg, Md.).

The data (Table IV) demonstrate that Strep A and Influenza A may be simultaneously measured in the same mucus-containing sample treated with nitrous acid. The effect of surfactant approximately doubled the viral assay signal, but has only a small effect on the Strep A assay.

TABLE IV

| | | Sample Treatment | |
|---|---|---|---|
| | | Nitrous acid/Tween | Nitrous Acid |
| Strep A | Positive Sample | 21384 | 16511 |
| | Negative Sample | 378 | 305 |
| Influenza A | Positive Sample | 1731 | 863 |
| | Negative Sample | 299 | 249 |

Example 6

Detection of Influenza A and Strep A Antigens in Clinical Samples Using Nitrous Acid Extraction Throat swabs were obtained from two individuals with Influenza A and two individuals with Strep A infections. The swabs were stored frozen at −20° C. After thawing, each swab was placed in 450 ul of freshly prepared extraction reagent and incubated for 1 minute, at which time the swab was removed and the solution neutralized by adding 50 ul of 2 M TRIS buffer (pH 7.5).

A Four-Spot Multi-Spot Plate was prepared with immobilized antibodies specific for Influenza A and Strep A on separate spots within each well. Another spot in each well was coated with BSA to serve as a background measurement. The neutralized swab extracts (75 ul) were combined with 10 ul of a mixture of TAG-labeled Influenza A and Strep A antibodies (final antibody concentrations were 1 ug/ml for each labeled antibody). The solution (50 ul) was dispensed into the wells and the plate was incubated for 8 minutes without mixing. The plate was then washed, assay buffer was added, and the amounts of Influenza A and Strep A were quantified by ECL (Table V). Surprisingly, markers of both viral particles and bacteria can be extracted simultaneously by the extraction reagent of the present invention.

TABLE V

| | ECL Signals (average of two replicates) | |
|---|---|---|
| | Antigen-specific spot | Background spot |
| Influenza A Sample 1 | 5269 | 808 |
| Influenza A Sample 2 | 6341 | 594 |
| Strep A Sample 1 | 54628 | 622 |
| Strep A Sample 2 | 27878 | 465 |

INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A kit for measuring a plurality of different organisms in a sample, the kit comprising:
   (a) a container, vessel or compartment comprising on a solid support:
      (i) a first binding reagent immobilized to a first region of said solid support, wherein said first binding reagent binds a first marker of a first organism from said plurality of different organisms and
      (ii) a second binding reagent immobilized to a second region of said solid support, wherein said second binding reagent binds a second marker of a second organism from said plurality of different organisms and
   (b) one or more additional containers, vessels or compartments comprising:
      (i) nitrous acid and a surfactant, together in one container, vessel or compartment, or
      (ii) an acid and a nitrite salt, as separate components, and a surfactant contained in each component or either component; wherein said first organism is a gram positive bacterium and said second organism is selected from the group consisting of fungi, viruses and gram negative bacteria.

2. The kit of claim 1, wherein said first and second binding reagents are antibodies.

3. The kit of claim 1, wherein said gram positive bacterium is a *Streptococcus* or *Enterococcus* bacterium and said first marker is a cell wall-associated antigen.

4. The kit of claim 3, wherein said gram positive bacterium is a *Streptococcus* Group A, B, F or G bacterium and said first marker is a group specific antigen.

5. The kit of claim 4, wherein said second marker is a protein, nucleic acid and/or lipid marker.

6. The kit of claim 1, wherein said solid support comprises a patterned array of antibodies immobilized thereon, said patterned array including said first region and said second region.

7. The kit of claim 1, further comprising a base or pH buffer for neutralizing said acid.

8. The kit of claim 1, wherein said kit includes said acid and nitrite salt and said nitrite salt and/or said acid is in a dry form.

9. The kit of claim 1, wherein said kit includes said acid and nitrite salt and said nitrite salt and/or said acid is in solution.

10. The kit of claim 1, wherein said kit includes nitrous acid.

11. The kit of claim 1, wherein components (a)-(b) are contained in an assay cartridge.

12. The kit of claim 1, wherein components (a)-(b) are contained in a mufti-well plate.

13. The kit of claim 1, further comprising an assay protocol for (i) extracting said sample with an extraction reagent comprising said nitrous acid or acid and nitrite salt and said surfactant, and for (ii) simultaneously measuring said first and second markers in an extracted sample.

14. A kit for measuring a plurality of different organisms in a sample, the kit comprising:
(a) a container, vessel or compartment comprising:
  (i) a first solid support comprising a first binding reagent immobilized thereto, wherein said first binding reagent binds a first marker of a first organism from said plurality of different organisms and
  (ii) a second solid support comprising a second binding reagent immobilized thereto, wherein said second binding reagent binds a second marker of a second organism from said plurality of different organisms; wherein said first organism is a gram positive bacterium and said second organism is selected from the group consisting of fungi, viruses and gram negative bacteria; and
(b) one or more additional containers, vessels or compartments comprising:
  (i) nitrous acid and a surfactant, together in one container, vessel or compartment, or,
  (ii) an acid and a nitrite salt, as separate components, and a surfactant contained in each component or either component.

15. The kit of claim 14, wherein said first and second binding reagents are antibodies.

16. The kit of claim 14, wherein said gram positive bacterium is a *Streptococcus* or *Enterococcus* bacterium and said first marker is a cell wall-associated antigen.

17. The kit of claim 16, wherein said gram positive bacterium is a *Streptococcus* A, B, F or G bacterium and said first marker is a group specific antigen.

18. The kit of claim 17, wherein said second marker is a protein, nucleic acid and/or lipid marker.

19. The kit of claim 14, wherein said first solid support and said second solid support each comprise a particle.

20. The kit of claim 14, further comprising a base or pH buffer for neutralizing said acid.

21. The kit of claim 14, wherein said kit includes said acid and nitrite salt and said nitrite salt and/or said acid is in a dry form.

22. The kit of claim 14, wherein said kit includes said acid and nitrite salt and said nitrite salt and/or said acid is in solution.

23. The kit of claim 14, wherein said kit includes nitrous acid.

24. The kit of claim 14, wherein components (a)-(b) are contained in an assay cartridge.

25. The kit of claim 14, wherein components (a)-(b) are contained in a mufti-well plate.

26. The kit of claim 14, further comprising an assay protocol for (i) extracting said sample with an extraction reagent comprising said nitrous acid or acid and nitrite salt and said surfactant, and for (ii) simultaneously measuring said first and second markers in an extracted sample.

27. A kit for measuring a plurality of different organisms in a sample, the kit comprising:
(a) a solid support comprising a first region and a second region, said support comprising:
  (i) a first binding reagent immobilized to said first region, wherein said first binding reagent binds a first marker of a first organism from said plurality of different organisms and
  (ii) a second binding reagent immobilized to said second region, wherein said second binding reagent binds a second marker of a second organism from said plurality of different organism types; wherein said first organism is a gram positive bacterium and said second organism is selected from the group consisting of fungi, viruses and gram negative bacteria; and
(b) one or more additional containers, vessels or compartments comprising:
  (i) nitrous acid and a surfactant, together in one container, vessel or compartment, or,
  (ii) an acid and a nitrite salt, as separate components, and a surfactant contained in each component or either component.

28. The kit of claim 27, wherein said first and second binding reagents are antibodies.

29. The kit of claim 27, wherein said gram positive bacterium is a *Streptococcus* or *Enterococcus* bacterium and said first marker is a cell wall-associated antigen.

30. The kit of claim 29, wherein said gram positive bacterium is a *Streptococcus* Group A, B, F or G bacterium and said first marker is a group specific antigen.

31. The kit of claim 30, wherein said second marker is a protein, nucleic acid and/or lipid marker.

32. The kit of claim 27, wherein said solid support comprises a particle.

33. The kit of claim 27, further comprising a base or pH buffer for neutralizing said acid.

34. The kit of claim 27, wherein said kit includes said acid and nitrite salt and said nitrite salt and/or said acid is in a dry form.

35. The kit of claim 27, wherein said kit includes said acid and nitrite salt and said nitrite salt and/or said acid is in solution.

36. The kit of claim 27, wherein said kit includes nitrous acid.

37. The kit of claim 27, wherein components (a)-(b) are contained in an assay cartridge.

38. The kit of claim 27, wherein components (a)-(b) are contained in a mufti-well plate.

39. The kit of claim 27, further comprising an assay protocol for (i) extracting said sample with an extraction reagent comprising said nitrous acid or acid and nitrite salt and said surfactant, and for (ii) simultaneously measuring said first and second markers in an extracted sample.

40. A kit for measuring a plurality of different organisms in a sample, the kit comprising:
(a) a first binding reagent that binds a first marker of a gram positive bacterium, wherein said first binding reagent is immobilized to a solid support;
(b) a second binding reagent that binds a second marker of an organism selected from the group consisting of fungi, viruses and gram negative bacteria, wherein said second binding reagent is immobilized to a solid support;
(c) one or more containers, vessels or compartments comprising:
(i) nitrous acid and a surfactant, together in on container, vessel or compartment, or,
(ii) an acid and a nitrite salt, as separate components, and a surfactant contained in each component or either component; and
(d) an assay protocol for (i) extracting said sample with the extraction reagent comprising said nitrous acid and said surfactant or said acid and nitrite salt and said surfactant, and for (ii) simultaneously measuring said first and second markers in the extracted sample.

41. The kit of claim 40, wherein said first and second binding reagents are antibodies.

42. The kit of claim 40, wherein said gram positive bacterium is a *Streptococcus* or *Enterococcus* bacterium and said first marker is a cell wall-associated antigen.

43. The kit of claim 42, wherein said gram positive bacterium is a *Streptococcus* Group A, B, F or G bacterium and said first marker is a group specific antigen.

44. The kit of claim 43, wherein said second marker is a protein, nucleic acid and/or lipid marker.

45. The kit of claim 40, wherein said solid support comprises a particle.

46. The kit of claim 40, further comprising a base or pH buffer for neutralizing said acid.

47. The kit of claim 40, wherein said kit includes said acid and nitrite salt and said nitrite salt and/or said acid is in a dry form.

48. The kit of claim 40, wherein said kit includes said acid and nitrite salt and said nitrite salt and/or said acid is in solution.

49. The kit of claim 40, wherein said kit includes nitrous acid.

50. The kit of claim 40, wherein components (a)-(c) are contained in an assay cartridge.

51. The kit of claim 40, wherein components (a)-(c) are contained in a mufti-well plate.

52. The kit of claim 40, wherein said first binding reagent is immobilized to a solid support comprising a magnetically responsive particle.

53. The kit of claim 40, wherein said second binding reagent is immobilized to a solid support comprising a magnetically responsive particle.

54. The kit of claim 40, wherein said first binding reagent is immobilized to a solid support comprising a first magnetically responsive particle and said second binding reagent is immobilized to a solid support comprising a second magnetically responsive particle.

* * * * *